United States Patent
Cook et al.

(10) Patent No.: US 6,821,436 B2
(45) Date of Patent: Nov. 23, 2004

(54) SEPARATION OF HALOGENATED COMPOUNDS

(75) Inventors: Kane David Cook, Eggertsville, NY (US); Charles Francis Swain, Williamsville, NY (US); Peter Brian Logsdon, Orchard Park, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/377,922

(22) Filed: Mar. 3, 2003

(65) Prior Publication Data

US 2003/0155305 A1 Aug. 21, 2003

Related U.S. Application Data

(63) Continuation of application No. 09/678,861, filed on Oct. 3, 2000, now abandoned.
(60) Provisional application No. 60/158,535, filed on Oct. 8, 1999.

(51) Int. Cl.[7] .......................... B01D 15/00; B01D 53/02; C07C 17/389
(52) U.S. Cl. ......................... 210/690; 95/142; 570/179
(58) Field of Search .......................... 95/142; 210/690; 570/179

(56) References Cited

U.S. PATENT DOCUMENTS 5,210,342 A * 5/1993 Moore ........................ 570/179
5,281,257 A * 1/1994 Harris .......................... 95/142
5,536,891 A   7/1996 Beard, Jr. .................... 570/262
5,608,129 A * 3/1997 Bertocchio .................. 570/179

OTHER PUBLICATIONS

"Polymeric Adsorbent XUS 43493" Dow Technical Bulletin 3.03.*
Dow Product Information Document—Polymeric Adsorbent XUS 43493 Technical Bulletin 3.03.
Dow Product Information Document—Dowex Optipore V493 Polymeric adsorbent for removal of organics from air streams, Dowex ion exchange resins and adsorbents.
Dow Product Information Document—Dowex Optipore Adsorbents Syrene Emissions Control.
Dow Product Information Document—Dowex Optipore L493 and V493 Dowex *Optipore* L493 and Dowex Optipore V493 Polymeric Adsorbent.
Dow Product Information Document—Dow Liquid Separations Dowex Optipore Adsorbents Fluidized Bed Properties of Dow Polymeric Adsorbents.

* cited by examiner

Primary Examiner—Ivars C. Cintins
(74) Attorney, Agent, or Firm—Colleen D. Szuch

(57) ABSTRACT

A process for removing a chlorinated methane impurity from a stream comprising a halogenated compound other than the chlorinated methane impurity, the process comprising contacting the stream with a polymer adsorbent to produce a purified product stream, the polymer adsorbent having a pore size distribution characterized by a higher cumulative porosity as a function of the log of pore diameter than that of activated carbon.

18 Claims, No Drawings

SEPARATION OF HALOGENATED COMPOUNDS

CROSS-REFERENCE TO RELATED APPLICATIONS

This application is a continuation of U.S. application Ser. No. 09/678,861 (now abandoned) which was filed with the U.S. Patent and Trademark Office on Oct. 3, 2000, and which, in turn, claims the benefit of U.S. Provisional Application No. 60/158,535 which was filed with the United States Patent and Trademark Office on Oct. 8, 1999.

FIELD OF INVENTION

This invention relates generally to a method for the separation of halogenated compounds, and, more specifically, to a method of removing the toxic impurity chlorofluoromethane (HCFC-31) from a product stream of difluoromethane (HFC-32).

BACKGROUND OF THE INVENTION

Historically, chlorofluorocarbons have been widely used in various capacities such as refrigerants, foam blowing agents, cleaning solvents and propellants for aerosol sprays. In recent years, however, there has been pressure to avoid their use due to their adverse effect on the ozone layer and their contribution to global warming. Consequently, attempts are underway to find suitable replacements which are environmentally acceptable. The search for suitable replacements has centered generally on hydrofluorocarbons (HFCs) which do not contain chlorine. The hydrofluorocarbon difluoromethane (HFC-32) is of particular interest as one such replacement. Difluoromethane has an ozone depletion potential (ODP) of zero and a very low global warming potential (GWP).

A widely-used method for preparing hydrofluorocarbons involves the fluorination of chlorinated starting materials. Unfortunately, fluorination of chlorinated staring materials usually results in the formation of unwanted, chlorinated by-products. For example, production of HFC-32 tends to produce a variety of chlorinated methane by-products including chlorodifluoromethane (HCFC-22), dichlorodifluoromethane (CFC-12), and chlorofluoromethane (HCFC-31). While distillation effectively removes many chlorinated impurities from an HFC product stream, some chlorinated impurities, particularly HCFC-31, cannot readily be removed through conventional distillation. Nevertheless, HCFC-31 must be removed to extremely low levels, for example, below 10 ppm, because it is highly toxic and tends to react with the desired HFC product.

Therefore, there is a need to remove chlorinated methane impurities, particularly HCFC-31, from a product stream more effectively then through distillation. The present invention fulfills this need among others.

DESCRIPTION OF THE INVENTION AND PREFERRED EMBODIMENTS

The present invention relates to the identification of a commercially-available polymer adsorbent that removes chlorinated methane impurities from a product stream. Although polymeric absorbents are known to remove organics from air and water (see, e.g., Dow Chemical Company, Polymeric Adsorbent XUS 43493, Technical Bulletin 3.03 (hereby incorporated by reference)), it has been found unexpectantly that the adsorbent of the present invention is particularly suitable for selectively adsorbing chlorinated methanes over halogenated compounds. In particular, the adsorbent of the present invention adsorbs chlorinated methanes, such as HCFC-31, but not hydrofluorocarbons, such as HFC-32.

One aspect of the present invention is a process of using a polymer adsorbent to remove a chlorinated methane impurity from an impure product stream comprising a halogenated compound other than the chlorinated methane impurity. In a preferred embodiment, the polymer adsorbent has a pore size distribution characterized by a cumulative porosity as a function of the log of pore diameter greater than that of activated carbon. In another preferred embodiment, the adsorbent comprises a matrix of at least one cross-linked styrenic polymer having a total porosity of at least about 0.8 cc/g, an average pore diameter of about 30 to about 60 Å, and a BET surface area of at least about 900 m²/g.

The process of the present invention has been found to be particularity effective in adsorbing a chlorinated methane impurity having the formula:

$$CH_wCl_yX_z \quad (1)$$

wherein: each X is an independently selected halogen; $y \geq 1$ and $w+y+z=4$.
Preferably X is fluorine. In a more preferred embodiment, the chlorinated methane impurity is selected from the group consisting of chlorofluoromethane (HCFC-31), dichloromethane (HCC-40), chlorodifluoromethane (HCFC-22), chlorotrifluoromethane (CFC-13), dichlorodifluoromethane (CFC-12) and combinations of two or more thereof. In the most preferred embodiment of the invention, the chlorinated methane impurity is HCFC-31.

In a preferred embodiment, separation is effected between a chlorinated methane of formula (1) and a halogenated compound having the following formula:

$$C_nH_mCl_pX'_k \quad (2)$$

wherein:
each X' is an independently selected halogen other than chlorine; and
n, m, p, and k are integers with the provisos that $1 \leq n \leq 10$; $n > p$; $k \geq 1$; and $2n+2=m+p+k$.
More preferably, $n \leq 3$, $p=0$, and X' is fluorine, and, even more preferably, $n=1$. In the most preferred embodiment, the product stream comprises HFC-32.

It is believed that pore distribution of the adsorbent may play a significant role in the selectivity described above. (The scope of the invention, however, should not be limited by any particular theory of adsorption). As used herein, "pore distribution" is a linear relationship between cumulative porosity and the log of the pore diameter. The preferred adsorbent of the present invention has pore distribution characterized by a higher cumulative porosity as a function of the log of pore diameter than that of activated carbon. In a more preferred embodiment, the pore size distribution is characterized by a cumulative porosity as a function of the log of pore diameter of no less than about 0.43 cc/g. Still more preferably, the cumulative porosity as a function of the log of pore diameter of no less than about 0.45 cc/g. The linear relationship of cumulative porosity to the log of pore diameter can vary, although a portion of the relationship is characterized by an exponential increase in cumulative porosity.

In a preferred embodiment, the absorbent comprises a matrix of at least one cross-linked styrenic polymer having a total porosity of at least about 0.8 cc/g, an average pore diameter of about 30 to about 60 Å, and a BET surface area of at least about 900 m²/g. More preferably, the total porosity is about 1.1 cc/g, average pore diameter is about 35 to about 55 Å, and BET surface area is at least about 1000 m²/g. Still more preferably, the total porosity is about 1.1 to about 1.2 cc/g, the average pore diameter is about 40 to about 50 Å, and the BET surface area is at least about 1100 m²/g. In the most preferred embodiment, the total porosity is about 1.16 cc/g, the average pore diameter is about 46 Å, and the BET surface area is about 1100 m²/g.

It has been found that polymeric adsorbents having relatively low moisture content tend to outperform equivalent adsorbents having relatively high moisture content. Accordingly, in a preferred embodiment, the moisture content is no greater than about 30% by weight, more preferably, no greater than about 10% by weight, and, even more preferably, no greater than about 5% by weight.

The configuration of the units of adsorbent may vary providing that the physical parameters above are met. It has been found, however, that spherical beads achieve the desired results. In a preferred embodiment, the beads have a diameter from about 10 to about 70 mesh, and, more preferably, from about 20 to about 50 mesh. Suitable results have been obtained using an adsorbent having an apparent density of about 0.20 to about 0.80 g/cc. Preferably, the apparent density is about 0.30 to about 0.70 g/cc, and, more preferably, about 0.34 g/cc.

Particular preferred and commercially-available polymeric adsorbents useful in the present invention includes DOWEX OPTIPORE 493 Series (available through Dow Chemical, Midland, Mich.), especially V493, which is described in detail in Dowex Optiore Adsorbents, Fluidized Properties of Dow Polymeric Adsorbent, Form No. 177-01731-597ORP (May 1997), herein incorporated by reference.

In the process of the invention, the product stream is contacted with the zeolite by passing the product stream over a fixed bed of polymeric absorbent in either the liquid or vapor phase. It has been found, however, that more effective removal of chlorinated methane impurities is achieved using a vapor-phase product stream. The bed should be packed tightly to ensure that very little, if any, vapor stream "breaks through" and passes through the bed without contacting the adsorbent sufficiently to promote adsorption. Selection of the pellet size and bed shape may be varied within a broad range and may be determined according to known principles, and, particularly, to provide the preferred densities described above. Various other techniques known in the art also may be used for contacting the product stream with the polymeric absorbent particles, including, for example, fluidized or moving beds of polymeric absorbent particles. Selection of the particle size and bed shape may be varied within a broad range and may be determined according to known principles, and, particularly, to provide the preferred pore distribution, porosity and/or surface area as described above.

The hourly space velocity of the product stream over the polymeric absorbent may be varied within a wide range. Generally, the product stream is passed over the active carbon with a gas hourly space velocity of about 5 to about 1000 h⁻¹, and preferably with a gas hourly space velocity of about 10 to about 500 h⁻¹, although the gas hourly space velocity may be much greater or much lower than this if desired. A corresponding liquid hourly space velocity for liquid phase operation is about 1 to about 30 h⁻¹, and, again, this velocity may be more or less if desired.

The conditions under which the process of the present invention is conducted may be varied widely and generally depend upon the equipment available. Typically, the temperature at which the vapor phase process is conducted is between about −50 and about 100° C., more conveniently, between about 0 and about 50° C., and even more conveniently at about room temperature. The pressure will be dependent to some extent upon whether liquid or vapor phase contacting is chosen and the operation temperature, although an operation pressure between about 0.1 and about 30 bar is generally suitable. Preferably, the process is conducted at about atmospheric pressure or slightly below to avoid the use of specialized equipment.

The bed of polymeric absorbent will require regeneration to desorb the chlorinated impurity when its absorption capacity has been filled. Regeneration may be performed by passing a gas stream, typically nitrogen or air, over the bed of polymeric absorbent at elevated temperature, for example, from about 50 to about 150° C., and preferably below about 100° C.

According to the process of the present invention, chlorinated methane impurities can be effectively removed from a product stream with high selectivity. The process of the present invention is particularly well suited for removing HCFC-31 from a product stream comprising HFC-32. For example, it has been found that the process of the present invention can be used to purify a vaporized product stream having a space velocity of no greater than about 100 hr⁻¹ in a tube packed with adsorbent of the present invention over a period of no greater than about 4 hours to result in a purified product stream containing less than 10 ppm of HCFC-31.

The following examples serve to illustrate the invention:

EXAMPLE 1

A 0.5 inch diameter by 19 inch long Teflon tube was packed with DOWEX OPTIPORE V493 to a bed height of approximately 16.5 inches. The tubes were sealed with glass wool on top and bottom of the bed so that the bed could not move. The bottom of the tube was fitted with connections to accommodate a feed of an impure product stream comprising HFC-32 and 549 ppm of HCFC-31 at a rate of 13.8 g/hr. The top of the tube was fitted with connections so that the purified product stream could be collected as it exited into cold traps. The HCFC-31 concentration dropped to 142 ppm after one hour of flowing the feed gas through the bed.

EXAMPLE 2

Example 1 was repeated, except adsorbent used was DOWEX OPTIPORE L493 and the flow of the feed gas mixture was at a rate of 5.30 g/hr. The HCFC-31 concentration was down to 7 ppm after four hours of flowing the feed gas through the bed.

What is claimed is:

1. A process for purifying a stream comprising contacting a stream comprising (a) a halogenated compound of the formula:

$$C_nH_mCl_pX'_k$$

wherein each X' is an independently selected halogen other than chlorine; m, n, and p are integers with the provisos that: $1 \geq n \geq 10$; n>p; $k \geq 1$; $m \geq 1$; and 2n+2=m+p+k and (b) a chlorinated methane impurity other than said halogenated compound with a polymer adsorbent to reduce the level of said chlorinated methane impurity relative to the level of said halogenated compound in said stream, said polymer adsorbent having a pore size distribution characterized by a higher cumulative porosity as a function of the log of pore diameter than that of activated carbon.

2. The process of claim 1, wherein said polymer adsorbent comprises a matrix of at least one cross-linked styrenic polymer.

3. The process of claim 2, wherein said chlorinated methane impurity has the formula:

wherein each X is an independently selected halogen; w, y, and z are integers with the provisos that: $y \geq 1$ and $w+y+z=4$.

4. The process of claim 3, wherein X is fluorine.

5. The process of claim 4, wherein said chlorinated methane impurity is $CH_2ClF$.

6. The process of claim 5, wherein said stream has a space velocity of no greater than about 100 $hr^{-1}$ over a period of no greater than about 4 hours to result in a purified stream containing less than about 10 ppm of HCFC-31.

7. The process of claim 1, wherein X' is fluorine, p=0, and $n \leq 3$.

8. The process of claim 7, wherein the halogenated compound is HFC-32.

9. The process of claim 1, wherein said pore size distribution is characterized by the cumulative porosity as a function of the log of pore size being no less than about 0.43 cc/g.

10. The process of claim 1, wherein said pore size distribution is characterized by a cumulative porosity that increases exponentially as a function of the log of pore diameter.

11. A process for purifying a stream comprising:

contacting a stream comprising (a) a halogenated compound of the formula:

wherein each X' is an independently selected halogen other than chlorine; m, n, and p are integers with the provisos that: $1 \geq n \geq 10$; n>p; $k \geq 1$; $m \geq 1$; and $2n+2=m+p+k$ and (b) a chlorinated methane impurity other than said halogenated compound with a polymeric adsorbent to reduce the level of said chlorinated methane impurity relative to the level of said halogenated compound in said stream, said polymeric adsorbent comprising a matrix of at least one cross-linked styrenic polymer having a total porosity of at least about 0.8 cc/g, an average pore diameter of about 30 to about 60 Å, and a BET surface area of at least about 900 $m^2/g$.

12. The process of claim 11, wherein said total porosity is about 1.1 to about 1.2 cc/g, average pore diameter is about 40 to about 50 Å, and BET surface area is at least about 1100 $m^2/g$.

13. The process of claim 12, wherein said total porosity is about 1.16 cc/g, average pore diameter is about 46 Å, and BET surface area is about 1100 $m^2/g$.

14. The process of claim 13, wherein said adsorbent is in the form of particles having a diameter of about 10 to about 70 mesh.

15. The process of claim 11, wherein said chlorinated methane impurity has the formula:

wherein each X is an independently selected halogen; w, y, and z are integers with the provisos that: $y \geq 1$ and $w+y+z=4$.

16. The process of claim 15, wherein said chlorinated methane impurity is $CH_2ClF$.

17. The process of claim 11, wherein X' is fluorine, p=0, and $n \leq 3$.

18. The process of claim 17, wherein the halogenated compound is HFC-32.

* * * * *